(12) United States Patent
Nataloni et al.

(10) Patent No.: US 11,814,691 B2
(45) Date of Patent: Nov. 14, 2023

(54) SEMI-CRYSTALLINE FRUCTOSE IN SOLID FORM AND PROCESS FOR MANUFACTURING THE SAME

(71) Applicant: CARGILL, INCORPORATED, Wayzata, MN (US)

(72) Inventors: Luigi Nataloni, Bologna (IT); Angelo Chianese, Rome (IT); Marco Stoller, Rome (IT)

(73) Assignee: Cargill, Incorporated, Wayzata, MN (US)

( * ) Notice: Subject to any disclaimer, the term of this patent is extended or adjusted under 35 U.S.C. 154(b) by 26 days.

(21) Appl. No.: 17/263,970

(22) PCT Filed: Jul. 30, 2019

(86) PCT No.: PCT/US2019/044133
§ 371 (c)(1),
(2) Date: Jan. 28, 2021

(87) PCT Pub. No.: WO2020/028360
PCT Pub. Date: Feb. 6, 2020

(65) Prior Publication Data
US 2021/0310087 A1    Oct. 7, 2021

(30) Foreign Application Priority Data
Jul. 30, 2018  (EP) ...................................... 8186370

(51) Int. Cl.
*C13K 11/00*  (2006.01)
(52) U.S. Cl.
CPC .................... *C13K 11/00* (2013.01)

(58) Field of Classification Search
CPC .......... A23P 10/40; A23P 10/43; A23P 20/12; A23P 20/00; C07H 1/00; C07H 3/02; C13K 11/00
USPC ......................................................... 127/30
See application file for complete search history.

(56) References Cited

U.S. PATENT DOCUMENTS

| 3,513,023 A | 5/1970 | Kusch |
| 3,929,503 A | 12/1975 | Yamauchi |
| 3,956,009 A | 5/1976 | Lundquist, Jr. |
| 4,517,021 A | 5/1985 | Schollmeier |

(Continued)

FOREIGN PATENT DOCUMENTS

| EP | 0195610 A2 | 9/1986 | |
| WO | 03016577 W | 2/2003 | |
| WO | WO-2015028784 A | * 3/2015 | ......... A23L 1/22008 |

OTHER PUBLICATIONS

Ludwig: amorphous matrix [online], [retrieved on Feb. 12, 2022]. Retrieved from the internet: <URL: https://ludwig.guru/s/amorphous+matrix> (Year: 2022).*

(Continued)

*Primary Examiner* — Stefanie J Cohen
*Assistant Examiner* — Ritu S Shirali

(57) ABSTRACT

A fructose in solid form containing a matrix and a plurality of carbohydrate crystals within said matrix, the matrix containing amorphous fructose and water, wherein the carbohydrate crystals comprise fructose and optionally one or more other carbohydrate(s), and optionally wherein the fructose in solid form is coated with a dry powder coating.

16 Claims, 1 Drawing Sheet

(56) References Cited

U.S. PATENT DOCUMENTS 4,681,639 A 7/1987 Hinck
4,938,804 A 7/1990 Heikkila

OTHER PUBLICATIONS

ISM: Mesh and Micron Sizes [online], [retrieved on Apr. 21, 2022]. Retrieved from the internet: < URL: https://www.industrialspec.com/resources/mesh-and-micron-sizes/> (Year: 2022).*
Collins, Definition of 'powder' [online], [retrieved on Apr. 22, 2022]. Retrieved from the internet: < URL: https://www.collinsdictionary.com/us/dictionary/english/powder > (Year: 2022).*

\* cited by examiner

SEMI-CRYSTALLINE FRUCTOSE IN SOLID FORM AND PROCESS FOR MANUFACTURING THE SAME

CROSS-REFERENCE TO RELATED APPLICATIONS

This application is a national phase of International Patent Application No. PCT/US2019/044133, filed Jul. 30, 2019, which claims the benefit of European Patent Application No. 18186370.5, filed Jul. 30, 2018, each of which is hereby incorporated by reference herein in its entirety.

FIELD OF THE INVENTION

The present invention relates to solidified fructose, to a process for producing solidified fructose and various uses of the solidified fructose e.g. in food, feed, personal care, pharmaceutical and industrial applications.

BACKGROUND OF THE INVENTION

Fructose is a monosaccharide also known as fruit sugar. Fructose has a higher sweetness than that of sucrose, and although it has the same caloric value as sucrose, due to its higher sweetness, it can be used in lesser amounts to obtain a similar sweetness than when sucrose is used.

Commercially, fructose is typically produced by isomerization of glucose. However, various challenges exist not only in the manufacture but also in the supply chain of fructose and in particular when the fructose is used in the food or pharmaceutical industry.

In the food and pharmaceutical industry, fructose is generally used in the form of fructose syrups containing between 9 and 90% by weight of fructose. Syrups having a low content of fructose (e.g. below 9 wt %) and consequently a high content of water, are less preferred by these industries since shipping them might imply higher transportation costs. The syrups typically have short shelf life, which may be due to instability, and may be affected by fructose crystallization, in particular during storage. Such crystallization is detrimental to the end user in that it changes the fructose content of the product that remains in syrup form and consequently it may become harder to handle. In particular dosing a syrup containing crystallized fructose may be increasingly difficult and may render a product containing thereof, heterogeneous.

Fructose is also available in solid form, as crystalline fructose or as semi-crystalline fructose. Crystalline fructose is typically a free-flowing product and consists essentially of fructose crystals with no amorphous formations. For many applications, fructose in solid, powder form is preferred, and sometimes even required, as it is easier to handle, store and dose than fructose syrups.

Crystalline fructose is produced by a number of well-known processes, including the so-called Starcosa process, described in U.S. Pat. No. 4,681,639, and those described in WO 03/016577, U.S. Pat. Nos. 3,513,023 and 4,938,804.

A number of prior-art processes describe the production of semi-crystalline fructose. Semi-crystalline fructose refers to fructose having crystalline fructose and amorphous fructose, typically in a ratio of about 1:1, usually the crystalline fructose content is much higher than the content of amorphous fructose.

U.S. Pat. No. 4,517,021 relates to semi-crystalline fructose product comprising less than about 2 wt % water and greater than about 60 weight % of crystalline fructose.

U.S. Pat. No. 3,929,503 relates to the preparation of anhydrous free-flowing solid particles of fructose by mixing crystalline fructose with fructose syrup and wherein the quantities of crystalline fructose used a much higher than the quantities of the fructose syrup, for example in a ratio crystalline fructose to fructose syrup of 4:0.4 or 4:1.55.

U.S. Pat. No. 4,681,639 relates to a process for producing a flowable dry product made of isoglucose syrup.

U.S. Pat. No. 3,956,009 relates to a process for preparing dried, solid, particulate fructose products from fructose solutions by drying the solution in a current of heated air and in the presence of separately introduced recycled dried product solids.

EP 0 195 610 describes a continuous process for the crystallization of fructose from an aqueous fructose syrup containing at least 90% by weight fructose on a dry solids basis, in which the syrup at a total solids content of at least 95% by weight is rapidly and thoroughly mixed with seed (fructose), at a temperature of 55-75 C e.g. for up to 2 minutes; is then deposited on a surface where it is allowed to crystallize under quiescent conditions at a temperature of 50-70 C, until a solid cake is formed; and is then comminuted to provide a free-flowing granular product which can be further dried.

Fructose crystallization processes are, however, difficult to operate, time-consuming, rather expensive and often result in a low yield of fructose and a large number of by-products, a so-called mother liquor. These disadvantages limit the use of crystalline fructose in food and pharmaceutical products.

There is thus a need for fructose in solid form, in particular in powder form, that can be produced in a more cost- and/or time-efficient manner. In particular, there is a need for a high-yield process for producing solid fructose, preferably in continuous mode, and in particular a solid fructose powder. There is also a need for cost- and/or time-efficient, high-yield processes, which produce solid fructose of high fructose purity or a solid fructose of specific properties, for example by adding other carbohydrates. There is also a need for such a process to yield a solid fructose powder with long-term stability (its properties do not substantially change with time) and easy handling (e.g. good flowability).

The present invention seeks to mitigate or alleviate the drawbacks of the prior art and to provide an improved fructose product and an optimized process for manufacturing thereof.

SUMMARY OF THE INVENTION

The invention relates to a fructose in solid form containing a matrix and a plurality of carbohydrate crystals within said matrix, the matrix containing amorphous fructose and water, wherein the carbohydrate crystals comprise fructose and optionally one or more other carbohydrate(s), and wherein the fructose in solid form is optionally coated with a dry powder coating.

Preferably, the one or more other carbohydrate(s) are selected from sweeteners and polyols. More preferably the one or more other carbohydrate(s) have a glass transition temperature (Tg) higher than the Tg of fructose.

However, if the carbohydrate crystals consist of (or contain only) crystals of fructose, then the fructose in solid form is preferably coated with a dry powder coating, preferably with a dry powder coating that is different from or does not consist of (or contain only) fructose.

The invention also relates to a fructose in solid form containing a matrix and a plurality of fructose crystals within said matrix, the matrix containing amorphous fructose and water, wherein the fructose in solid form is preferably coated with a dry powder coating, preferably with a dry powder coating that is different from or does not consist of (or contain only) fructose.

The invention also relates to a powder containing particles, the particles comprising the fructose in solid form.

The inventors observed that the fructose in solid form in accordance with the invention, hereinafter "the inventive fructose", can be produced in a time- and cost-efficient manner. In addition, the inventive fructose is of a high purity, good flowability and long-term stability. By adding other carbohydrates it is also possible to obtain other specific properties of the inventive fructose, also with good flowability and long-term stability.

The invention, further relates to a method of manufacturing solidified fructose, in particular the inventive fructose, comprising:
(i) Providing an aqueous fructose solution having a dry substance (DS) of at least 80 wt % relative to the total mass of the solution;
(ii) Providing a powder containing particles comprising a carbohydrate material;
(iii) Adding the powder to the aqueous fructose solution to obtain an aqueous slurry having a glass transition temperature ($T_g$);
(iv) Cooling the aqueous slurry to a temperature of at most the $T_g$ of said slurry thereby obtaining a product containing solidified fructose;
(v) Optionally milling the product containing the solidified fructose and/or coating the solidified fructose or the milled solidified fructose.

The inventors observed that the process in accordance with the invention, hereinafter "the inventive process", can produce the inventive fructose in a cost- and time-efficient manner but also in high yield. In particular, the inventive process may be designed to run with increased efficiency in the sense that it may use a low amount of energy and/or the amount of waste material (e.g. mother liqueour) may be kept to a minimum and even to zero waste. Consequently, there may be no need of a recycling step of waste streams in the inventive process. Furthermore, the obtained solid fructose powder is stable and can be handled easily. Other advantages of the invention will become apparent from the detailed description given hereunder.

The invention further relates to a food, feed, personal care, pharmaceutical or industrial product comprising the inventive fructose.

The invention further relates to the inventive fructose obtainable according to the inventive process.

DETAILED DESCRIPTION OF THE INVENTION

Figure 1:
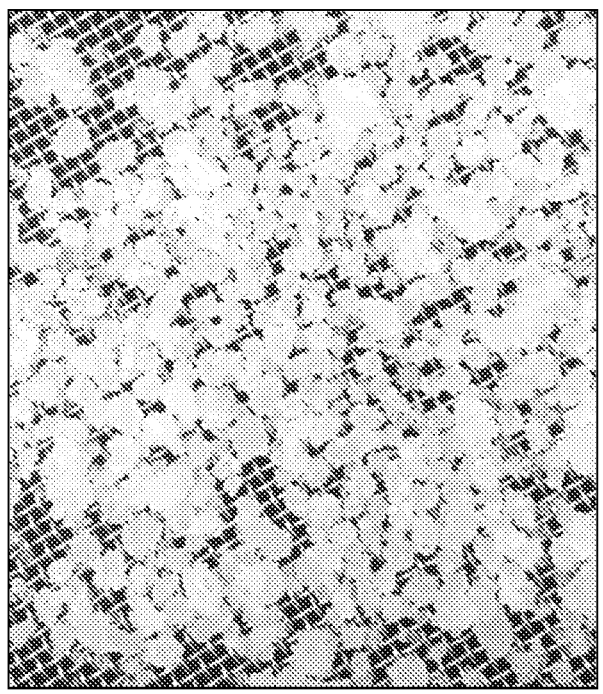
FIG. 1 is an image of the semi-crystalline fructose obtained by the inventive process described herein.

The invention relates to a fructose in solid form containing a matrix phase and a dispersed phase, the dispersed phase being dispersed within said matrix, the matrix phase containing amorphous fructose and the dispersed phase containing a plurality of carbohydrate crystals, wherein optionally the fructose in solid form is coated with a dry powder coating.

The carbohydrate crystals can be crystals comprising fructose and optionally one or more other carbohydrate(s). Preferably, the one or more other carbohydrate(s) have a glass transition temperature (Tg) higher than the Tg of fructose.

However, if the carbohydrate crystals consist of (or contain only) crystals of fructose, then the fructose in solid form is preferably coated with a dry powder coating, wherein the dry powder coating preferably is different from or does not consist of (or contain only) fructose.

The invention also relates to a fructose in solid form, containing a matrix phase and a dispersed phase, the dispersed phase being dispersed within said matrix, the matrix phase containing amorphous fructose and the dispersed phase containing a plurality of fructose crystals. In such a case, where the carbohydrate crystals consist of (or contain only) crystals of fructose, the fructose in solid form is preferably coated with a dry powder coating, preferably with a dry powder coating that is different from or does not consist of (or contain only) fructose.

The invention also relates to a powder containing particles comprising the inventive fructose.

The following applies to all of the inventive fructose disclosed herein:

The inventive fructose is in solid form, i.e. said fructose can essentially retain its shape for at least 1 hour when placed on a flat surface at a temperature less than 40° C. and at a relative humidity less than 80%. The inventive fructose may have any regular or irregular shape, e.g. powder, fibres, a block, and the like.

The inventive fructose contains a matrix phase and a dispersed phase. The matrix phase is herein understood a continuous phase embedding the dispersed phase. The dispersed phase is dispersed, preferably homogeneously, inside the matrix phase.

Preferably, the matrix phase is present in an amount of at least 85% DS, more preferably at least 90% DS, even more preferably at least 95% DS and most preferably said amount is at most 99% DS.

The matrix phase of the inventive fructose contains amorphous fructose. By amorphous fructose is herein understood a solid formed at non-equilibrium conditions either by removing the dispersing medium (such as water), or from the melt by cooling, or by rapid supercooling. This material is not at thermodynamic equilibrium, and therefore is unstable relative to the crystalline form. The amorphous fructose is preferably present in an amount of at least 0.1 wt % relative to the total mass of the inventive fructose, more preferably at least 5.0 wt %, most preferably at least 10.0 wt %. Preferably, said amount of amorphous fructose is at most 80 wt %, more preferably at most 30 wt %, most preferably at most 25 wt %. Preferably, said amount of amorphous fructose is between 0.1 wt % and 80 wt %, more preferably between 5 wt % and 25 wt %, most preferably between 10 wt % and 15 wt %.

The matrix phase may also contain water. The water is preferably present within the matrix phase in an amount of preferably at least 0.2 wt % relative to the total mass of the inventive fructose, more preferably at least 2.0 wt %, most preferably at least 5.0 wt %. Preferably, said amount of water is at most 20 wt %, more preferably at most 15 wt %, most preferably at most 10 wt %. Preferably, said amount of water is between 0.2 wt % and 20 wt %, more preferably between 2 wt % and 15 wt %, most preferably between 5 wt % and 10 wt %.

The matrix phase may also contain impurities typically in an amount of between 1 and 20 wt %. These may be impurities initially present in the fructose solution or introduced during the manufacturing process.

The dispersed phase is distributed inside the matrix phase, said dispersed phase containing carbohydrate crystals comprising fructose crystals and optionally one or more other carbohydrate(s). By being distributed inside the matrix phase it is herein understood that the crystals are distributed or dispersed inside said matrix phase. Said crystals may be present inside the matrix phase as singular crystals or as clusters of crystals or combinations thereof. By crystals is herein understood as including the solid material (preferably carbohydrate material) added to the solution to give rise to the aqueous slurry of step iii. This slurry may enhance the crystallization of the solute fructose in the matrix phase. The dispersed phase is preferably present in an amount of at least 3 wt % relative to the total mass of the inventive fructose, more preferably at least 5 wt %, 10 wt %, 15 wt % or 20 wt %, even more preferably at least 70 wt %, most preferably at least 75 wt %. Preferably, said amount of carbohydrate crystals, including fructose crystals, is at most 99.8 wt %, more preferably at most 90 wt %, most preferably at most 80 wt %. Preferably, said amount of carbohydrate crystals, including fructose crystals, is between 3 wt % and 99.8 wt %, more preferably between 5 wt %, 10 wt %, 15 wt % or 20 wt % and 99.8 wt %, even more preferably between 70 wt % and 90 wt %, most preferably between 75 wt % and 80 wt %. The amount of crystals will depend on the particle size of the crystals, as is known to a person skilled in the art.

The one or more other carbohydrates can be present from at least 1, 3, 5, 10, 15, 20, 30, 40, 50, 60, 70, 80, 90, 92, 95, 97, 98, 99 or 99.5 wt % of the total amount of carbohydrate crystals present in the inventive fructose. The one or more other carbohydrates can be present at at most 99.5, 99, 98, 97, 95, 92, 90, 80, 70, 60, 50, 40, 30, 20, 15, 10, 5, 3 or 1 wt % of the of the total amount of carbohydrate crystals present in the inventive fructose.

The carbohydrate crystals can be crystals comprising fructose and optionally one or more other carbohydrate(s). Preferably, the one or more carbohydrate(s) are selected from sweeteners and/or polyols. Preferably the sweetener is selected from dextrose, maltose, isomaltuose, mannose, sucrose, lactose, trehalose, galactose, raffinose and mixtures thereof. Preferably the polyol is selected from sorbitol, xylitol, erythritol, maltitol, isomalt, isomaltitol, mannitol and mixtures thereof. More preferably, the one or more carbohydrate(s) are selected from carbohydrates having a glass transition temperature (Tg) higher than the Tg of fructose. Most preferably the sweetener is selected form dextrose, sucrose, maltose, isomaltuose, lactose, raffinose and mixtures thereof. Most preferably the polyol is selected from maltitol, isomalt, mannitol and mixtures thereof. Preferably the carbohydrate crystals, which have been added during the seeding process (i.e. in step iii), are different from or do not consist of (or contain only) crystals of fructose.

If the carbohydrate crystals consist of (or contain only) crystals of fructose, then the fructose in solid form is preferably coated with a dry powder coating, wherein the dry powder coating preferably is different from fructose or does not consist of (or contain only) fructose. Suitable coating material is described below and will not be repeated here.

The matrix phase and/or the dispersed phase may further contain internally, various carbohydrates, non-limiting examples thereof including dextrose, maltose, sorbitol, *stevia* and mixtures of one or more thereof. Further examples of suitable carbohydrate materials are given herein below. By "containing internally" it is herein understood that the carbohydrates are present inside said phases, i.e. in the bulk. If present, the carbohydrate material is preferably comprised in an amount of at most 49 wt % DS, relative to the total combined amount of the matrix and dispersed phases, preferably at most 25 wt % DS, more preferably at most 20 wt % DS, even more preferably at most 15 wt % DS, yet even more preferably at most 10 wt % DS, yet even more preferably at most 5 wt % DS, yet even more preferably at most 2 wt % DS, most preferably at most 1 wt % DS.

The inventive fructose is preferably in the form of a powder. The powder contains particles comprising the inventive fructose and preferably having a D50 of at least 10 µm, more preferably at least 50 µm, even more preferably at least 100 µm, most preferably at least 150 µm. Preferably, said DSO is at 2500 µm, more preferably at most 700 µm, even more preferably at most 300 µm, most preferably at most 200 µm. Preferably, said DSO is between 10 µm and 2500 µm, more preferably between 50 µm and 700 µm, most preferably between 150 µm and 200 µm.

Preferably, the particles have a D90 of preferably at least 20 µm, more preferably at least 80 µm, even more preferably at least 150 µm, most preferably at least 200 µm. Preferably, said D90 is at most 3000 µm, more preferably at most 1000 µm, even more preferably at most 500 µm. Preferably, said D90 is between 20 µm and 3000 µm, more preferably between 80 µm and 1000 µm, most preferably between 100 µm and 500 µm.

The particle size distributions D50 and D90 and the mean particle diameters (mean volume diameter of particle diameters: MV) of the particles forming the powder were measured by laser diffraction (Beckman Coulter, LS 13 320, Miami, Fla.) as detailed in the MEASURING METHODS section of the description.

Preferably, said particles are coated with a dry powder coating, which may advantageously provide said particles with non-stickiness abilities and may provide the powder with good flow properties. By dry powder coating is herein understood a coating in the form of a powder having a moisture content of at most 20 wt % based on the total weight of the powder. Preferably, the moisture content is at least 0.1 wt %, more preferably at least 1.0 wt %, even more preferably at least 2.0 wt %, most preferably at least 5.0 wt %. Preferably, said moisture content is at most 20 wt %, more preferably at most 15 wt %, most preferably at most 10 wt %. Preferably, said moisture content is between 0.1 wt % and 20 wt %, most preferably between 0.1 wt % and 10 wt %.

The dry powder coating contains coating particles, said coating particles having a D50 that is at least 15% smaller than the D50 of the particles forming the powder, more preferably at least 20% smaller, even more preferably at least 25% smaller, yet even more preferably at least 30% smaller, most preferably at least 35% smaller. Preferably, said coating particles are at most 75% smaller than the D50 of the particles forming the powder, more preferably at most 60% smaller, most preferably at most 60% smaller.

Any material may be used for the particles of the dry powder coating. This is preferably any material that can prevent water absorption and/or stickiness of the inventive fructose. Preferably, the coating particles contain a carbohydrate material. Non-limiting examples of the carbohydrate material include sweeteners, starches including modified starches, hydrocolloids, polyols, dextrins, maltodextrins, food-grade polymers, biopolymers and the like and mixtures thereof. Most preferred carbohydrate materials are sweeteners and polyols.

The sweetener may be a nutritive sweetener, a high intensity sweetener and mixtures thereof. Non-limiting examples of nutritive sweeteners include sucrose, maltose, lactose, glucose, and galactose. The nutritive sweetener may also be a fructose different than the inventive fructose, preferably a crystalline fructose with a crystallinity of above 95%. The high intensity sweetener may be selected among aspartame, acesulfame salts such as acesulfame-K, saccharins, cyclamates, sucralose, alitame, neotame, steviosides, glycyrrhizin, neohesperidin dihydrochalcone, monellin, thaumatin, brazzein and mixture of two or more thereof. Preferably the high intensity sweetener is *stevia*.

The polyol may be selected among the tetritols, pentitols, hexitols, hydrogenated disaccharides, hydrogenated trisaccharides, hydrogenated tetrasaccharides, hydrogenated maltodextrins and mixture thereof. More specifically, the polyol can be selected from the group consisting of erythritol, threitol, arabinitol, xylitol, ribitol, allitol, altritol, gulitol, galactitol, mannitol, sorbitol, talitol, maltitol, isomaltitol, isomalt, lactitol and mixtures of two or more thereof. Preferably the polyol is maltitol, sorbitol, isomalt or a mixture of two or more thereof.

In a preferred embodiment, the dry powder coating contains particle containing the inventive fructose and having a particle size distribution within the ranges described hereinabove in relation to said coating. The dry powder coating of this embodiment can be obtained by finely milling the inventive fructose.

Preferably, the dry powder coating contains particles comprising dextrose, *stevia*, sorbitol, fructose different than the inventive fructose, inventive fructose or mixtures thereof.

However, if the carbohydrate crystals consist of (or contain only) crystals of fructose, then the dry powder coating preferably is different from or does not consist of (or contain only) fructose, but may contain one or more of the materials mentioned for the dry coating above.

The invention further relates to a powder (hereinafter referred to as "the inventive powder") containing particles, said particles comprising the inventive fructose. Preferred embodiments of the particles are given hereinabove and will not be repeated herein.

Preferably the inventive powder has a moisture content of from 0.1 to 20.0 wt %.

The inventors observed that the inventive fructose and the inventive powder are highly soluble, they can easily be dissolved in water at room temperature (at 20° C.) up to amounts of 3760 g/l. Preferably, the inventive fructose and the inventive powder have a solubility of at least 700 g/l, more preferably at least 1000 g/l, most preferably at least 3750 g/l.

The particles forming the inventive powder may also be in the form of agglomerates. If present, said agglomerates preferably have a mean diameter of from 0.2 to 10 mm, more preferably from 0.3 to 5 mm, most preferably from 0.8 to 1.5 mm Mean diameter may be measured by means of a sieving procedure and/or dimensional analysis of images under an optical microscope.

The inventors surprisingly observed that the inventive fructose has a white colour, i.e. it is characterized by a CIELAB L* value of at least 85, more preferably at least 90, most preferably at least 95. Preferably, the CIELAB b* value is at most 100, more preferably at most 99, most preferably at most 98.

The inventors surprisingly observed that the inventive powder has an optimum flowability. Preferably, the flowability of said powder is between 20 and 45 degrees [Angle of response], more preferably between 25 and 45, most preferably between 30 and 35.

The inventors surprisingly observed that the inventive powder and/or the inventive fructose may have an optimum hydrophilicity. Preferably, the hydrophilicity thereof is between 15% and 50% [mass increase at standard test conditions], more preferably between 20% and 45%, most preferably between 30% and 40%.

The invention, further relates to a method of manufacturing solidified fructose, in particular the inventive fructose, (hereinafter the "inventive method") comprising:
(i) Providing an aqueous fructose solution having a dry substance (DS) of at least 80 wt % relative to the total mass of the solution;
(ii) Providing a powder containing particles comprising a carbohydrate material;
(iii) Adding the powder to the aqueous fructose solution to obtain an aqueous slurry having a glass transition temperature ($T_g$);
(iv) Cooling the aqueous slurry to a temperature of at most the $T_g$ of said slurry thereby obtaining a product containing solidified fructose;
(v) Optionally milling the product containing the solidified fructose and/or coating the solidified fructose or the milled solidified fructose.

The aqueous fructose solution of step (i) preferably has a DS of at least 85 wt %, more preferably at least 90 wt %. Preferably said DS is from 90 to 99.9 wt %, more preferably from 94 to 98 wt %, most preferably from 96 to 98 wt %.

Preferably, the temperature of the aqueous fructose solution is from 50° C. to 90° C., more preferably from 50 to 70° C., even more preferably from 55 to 65° C. Preferably, the aqueous fructose solution is maintained at such temperature under constant or regular stirring. Preferably, the aqueous fructose solution is kept under conditions such that the DS does not change. Any suitable means to maintain the aqueous fructose at a said temperature may be used and any suitable means of stirring may be used.

The aqueous fructose solution may be obtained for example by concentration of a less concentrated aqueous fructose solution such as an aqueous fructose solution having a DS content being less than the DS content of the aqueous fructose solution of step (i). For example, said less concentrated aqueous fructose solution may have a DS content of from 10 wt % to less than 80 wt %, or from 20 wt % to 70 wt %, or from 30 wt % to 50 wt %, or from 35 wt % to 45 wt %. Said less concentrated aqueous fructose solution preferably has a fructose purity of from 40 to 95 wt %, preferably from 50 to 95 wt %, more preferably from 70 to 95 wt %, even more preferably from 80 to 95 wt %, yet even more preferably from 90 to 95 wt %. By fructose purity it is herein understood fructose mass per overall DS mass.

Concentration of the less concentrated aqueous fructose solution may be done by evaporation. Evaporation may be done by heating said less concentrated fructose solution at a temperature suitable to remove water without affecting the physical properties of the fructose in the solution, e.g. under vacuum. The evaporation temperature may be for example from 50 to 90° C., preferably from 50 to 70° C., more preferably from 55 to 65° C. Heating may be carried out in a double jacketed vessel using water or any higher boiling point fluid as heating medium. Preferably heating is done in a closed system from which water is removed in a controlled manner in order to obtain the desired DS. Preferably, stirring is applied during heating. More preferably continuous stirring is applied.

In step (ii) of the inventive method, a powder containing particles comprising a carbohydrate material is provided. The particles preferably have a diameter (considering said particles spheres) of preferably at most 3 mm, more preferably at most 2 mm Preferably said diameter is at least 150 μm, more preferably at least 500 μm, even more preferably at least 1500 μm.

The carbohydrate material may comprise or consist of one or more carbohydrate(s). The powder may thus contain particles, which comprise or consist of one or more carbohydrate(s).

The carbohydrate material may comprise or consist of fructose and optionally one or more carbohydrate(s). The powder may thus contain particles, which comprise or consist of fructose and optionally one or more carbohydrate(s).

The carbohydrate material may comprise or consist of one or more carbohydrate(s) excluding fructose. The powder may thus contain particles, which comprise or consist of one or more carbohydrate(s) excluding fructose.

The carbohydrate material may comprise or consist of one or more carbohydrate(s), which have a glass transition temperature (Tg) higher than the Tg of fructose. The powder may thus contain particles, which comprise or consist of one or more carbohydrate(s), which have a glass transition temperature (Tg) higher than the Tg of fructose.

Preferably, the one or more carbohydrate(s) are selected from sweeteners and/or polyols. Preferably the sweetener is selected from fructose, dextrose, maltose, isomaltuose, mannose, sucrose, lactose, trehalose, galactose, raffinose and mixtures thereof. Preferably the polyol is selected from sorbitol, xylitol, erythritol, maltitol, isomalt, isomaltitol, mannitol and mixtures thereof. More preferably, the one or more carbohydrate(s) are selected from carbohydrates having a glass transition temperature (Tg) higher than the Tg of fructose. More preferably the sweetener is selected form dextrose, sucrose, maltose, isomaltulose, lactose, raffinose and mixtures thereof. More preferably the polyol is selected from maltitol, isomalt, mannitol and mixtures thereof.

Further suitable examples of the carbohydrate material are given hereinabove in reference to the dry powder coating and will not be repeated herein. Preferably, said material is one or more nutritive sweeteners, one or more polyols (e.g. sorbitol), one or more high intensity sweeteners (e.g. *stevia*) or mixtures thereof. Most preferably, said carbohydrate material is the inventive fructose and/or the inventive powder, most preferably the inventive powder. When the inventive fructose and/or the inventive powder is/are used, the process may use any of the other carbohydrate materials to produce said powder and/or said fructose in a suitable quantity for being used in step (ii) of the inventive method.

At step (iii) of the inventive method, the powder is added to the aqueous fructose solution to obtain an aqueous slurry. Preferably, the addition is done by mixing. Mixing is preferably carried out to achieve a homogeneous slurry, i.e. a slurry wherein the powder is homogeneously distributed. Mixtures and in particular homogeneous mixtures can be achieved by mixing the said powder and said solution at preferably constant temperature. Preferably, step (iii) is carried out at a temperature of at least 60° C., more preferably at least 65° C., even more preferably at least 68° C., most preferably at least 70° C. Preferably, said solution temperature is at most 90° C., more preferably at most 85° C., even more preferably at most 80° C., most preferably at most 75° C. Preferably, step (iii) is carried out by mixing at a temperature as indicated hereinabove. Mixing can be carried out with any mixing device known in the art such as for example a static mixing device, a high-speed mixing device and the like.

Mixing can be carried out for a mixing time of at least 1 sec and up to 24 h. Preferably the mixing time is from 30 s to 40 minutes, more preferably from 1 minute to 30 minutes, even more preferably from 5 minutes to 20 minutes, most preferably from 15 minutes to 25 minutes.

During the mixing, the aqueous fructose solution and the powder are forming a slurry. The difference between a solution and a slurry is well known in the art, i.e. a slurry is a mixture containing the powder in solid phase dispersed within a liquid phase and may also contain dissolved powder. A solution on the other hand means that the powder is dissolved and essentially no solid-phase exists therein.

Step (iii) of the inventive method may also be referred to as 'seeding'. Seeding may induce fructose crystallization to some extent. Preferably the powder is mixed with the aqueous fructose solution in an amount of from 1 to 20 wt %, more preferably from 1 to 15 wt %, even more preferably from 1 to 10 wt %, yet even more preferably from 2 to 10 wt %, yet even more preferably from 3 to 10 wt %, yet even more preferably from 4 to 10 wt %, yet even more preferably from 5 to 10 wt %, most preferably from 8 to 10 wt %, based on the weight of the fructose solution provided in step (i).

The aqueous slurry is characterized by a glass transition temperature ($T_g$). The $T_g$ is the temperature at which a reversible transition occurs between a solid amorphous (glassy) state and a supercooled liquid (rubbery) state and is a parameter of critical importance to the stability of amorphous materials. $T_g$ can be measured by using differential scanning calorimetry (DSC). Typically, to determine $T_g$ a sample of the material is first cooled with 10 K/min and then heated with that same speed. For example, amorphous fructose, or non-crystalline fructose, is typically characterized by a glass transition temperature of between 7 and 17° C., however, it is well known that this temperature range can be significantly affected by the composition of the product as well as by the way of manipulation thereto (e.g. cooling). In particular, depending on the composition of the fructose slurry and the type of carbohydrate material used in the seeding step, the glass transition temperature can be varied. Preferably, the $T_g$ of the aqueous slurry of step (iii) of the inventive method is at least −20° C., more preferably at least −10° C., even more preferably at least −5° C., most preferably at least −2° C. Preferably, said $T_g$ is at most 5° C., more preferably at 10° C., even more preferably at most 20° C., most preferably at most 40° C.

In step (iv), the slurry is cooled to a temperature of at most the $T_g$ of said slurry, i.e. a temperature equal to or below said $T_g$. The aim of this step is to cause the formation of a product (a slurry containing solidified fructose) in a glassy state. Cooling to said temperature induces therefore the formation of solidified fructose inside the aqueous slurry and produces therefore a product containing said solidified fructose. The product may also contain water and the carbohydrate material.

Preferably, the aqueous slurry is cooled at a cooling temperature of at 1° C. below the $T_g$ of said slurry, more preferably of at least 3° C., even more preferably of at least 5° C., most preferably of at least 10° C. below the $T_g$ of said slurry.

Cooling is preferably performed under atmospheric conditions at controlled humidity in order to prevent condensation of ambient moisture. Preferably cooling is done in the presence of nitrogen or other inert gas. Preferably, the cooling is carried out in a cooling environment having a relative humidity of from 0 to 70%, more preferably from 0 to 10%, most preferably from 0 to 5%. Preferably, the cooling is rapid or quick cooling, i.e. quenching. The cooling is preferably carried out with a cooling of between 40 and 120° C./sec, more preferably of between 50 and 100° C./sec, most preferably of between 60 and 80° C./sec.

Cooling may be performed by feeding the aqueous slurry into or onto cooling means. Preferably, said cooling means is provided with means to keep the cooling temperature constant and continuously remove the solidification heat released during the solidification process.

The cooling means may be a refrigerated surface, such as a refrigerated belt or refrigerated (revolving) disk for example. The cooling means may also be a cooled gas stream e.g. a cooled air stream or a cooled stream of nitrogen.

Advantageously, the feeding of the aqueous slurry into or onto the cooling means, is done in such a way that the obtained solidified fructose is in the form of particles, threads or filaments. The particles, threads or filaments may be of various sizes, e.g. various diameters, lengths and widths.

Preferably the feeding is carried out such that particles or agglomerated particles are formed, said particles being preferably essentially spherical. If agglomerates are formed, the mean diameter of the agglomerates is preferably from 0.2 to 10 mm, more preferably from 0.3 to 5 mm, most preferably from 0.8 to 1.5 mm. To achieve such particles and/or agglomerates, the aqueous slurry may be fed to the cooling means in the form of droplets. Most preferably, cooling is done by feeding the aqueous slurry in the form of droplets onto a refrigerated belt.

After cooling, the product obtained may be milled in order to reduce its particle size to a desired particle size. Preferably, after milling, the product is obtained in the form of granules or agglomerates having a mean diameter of from 0.3 to 4 mm, more preferably from 0.8 to 1.5 mm Milling is thus not required in case the mean diameter of the agglomerates obtained after cooling is already in said range.

Milling can be done using standard milling apparatus such as fine cutting mills, externally refrigerated to operate below the glass transition temperature of the solidified product. Preferably also milling is performed under atmospheric conditions at controlled humidity. The relative humidity may be from 0 to 70%, preferably from 0 to 10%, more preferably from 0 to 5%.

After cooling, or after milling in case a milling step is performed, the solidified fructose may be coated with the dry powder coating described above in the present description. The temperature during the coating step does not need to be strictly controlled. It is increased at or above the glass transition temperature range, preferably up to the ambient temperature. After coating, the solidified fructose may be stored at ambient temperature or it may be refrigerated. Preferably it is stored under sealed conditions.

The present invention further relates to food, feed, personal care, pharmaceutical or industrial product comprising the solidified fructose of the present invention. The food product may be confectionery product, beverage, bakery, dairy, or frozen products. Solidified fructose may also be used as an excipient in pharmaceutical products such as powdered medicines, tablets and the like.

Methods of Measurement

Moisture content ("MC"): The moisture content was determined with an infrared moisture balance (MA30, Satorius). The sample was dried at 105° C. The moisture content (in wt %) was calculated as $(A1-A2)/A1 \times 100$ where $A1$ was the weight of the sample before drying in the oven and $A2$ was the weight of the resulted dried sample.

Dry substance content ("DS") is measured according to formula:

$$DS\ (\%) = 100\% - MC\ (\%)$$

Particle size distribution: The particle size distribution was measured by laser diffraction (Beckman Coulter, LS 13 320, Miami, Fla.). Samples were poured into a stirred tank, filled with pure ethanol and circulated 2 times into the measuring cell (pumping rate 30%). Laser light having 750 nm wavelength was used as the main laser light source, whereas laser light having wavelength of 450, 600, and 900 nm was used for polarization intensity differential scattering (PIDS). The detection range was 0.04-2000 µm. The volumetric particle size distributions of the samples were calculated from the intensity distributions of the scattered light according to the Fraunhofer optical model using the instrument's software (plant cell wall RI=1.6, water RI=1.33 and absorption coefficient for the dispersion 1) (Verrijssen et al., 2014).

Average particle size may be determined by ASTM C136-06.

Tg: A thermomechanical analysis (TMA) uses a small sample of material, which is heated on a quartz stage. A rod inside the machine places a small amount of force on the top of the sample, and the movement of the rod is measured with a linear variable differential transformer or LVDT. The entire instrument is heated at a slow rate, usually 5 degrees C. per minute. This data is reported as a curve, where change in length is plotted versus temperature. The slope of the resulting curve is called the coefficient of linear thermal expansion, or COLTE. The glass transition temperature is the point at which the slope of the line changes.

Microscopy Analysis: The microstructure of the non-homogenised and homogenised samples was visualised by means of microscopy, using specific dyes and epifluorescent lightening, as well as normal light. The epifluorescent samples were stained with acridine orange (dilution of 1:100 from 2% concentrated dye) and analysed using an Olympus BX-41 microscope, equipped with an Olympus XC-50 digital camera and photo-analysing software. Acridine orange was used as a cationic dye which associates with polyanionic compounds while emitting a green fluorescence.

Flowability measurement method: The angle of repose is the angle (relative to the horizontal base) of the conical pile produced when a granular material is poured on to a horizontal surface. It is related to the density, surface area and coefficient of friction of the material concerned. The angle of repose attachment comprises a 100 mm diameter circular test platform together with a digital height gauge having a range of 0-300 mm. For this particular test, the funnel is normally equipped with a special 10 mm i.d. nozzle mounted 75 mm above the test platform. The angle of repose can be determined by reading off the height of the powder cone in mm from the digital display of the height gauge and dividing the reading by 50.

Hydrophobicity measurement method: the degree of hygroscopicity of a substance is defined based on the percentage increase of mass of the substance after 24 hours of exposure at 80±2 percent relative humidity and 25±1° C.

A substance is extremely hygroscopic if the mass increase at the above conditions is equal or higher than 15%.

Measuring Color (CIELAB L*, b* values): CIE L*a*b* (CEILAB) is the most complete color space specified by the International Commission on Illumination (Commission Internationale d'Eclairage). It describes all the colors visible to the human eye and was created to serve as a device independent model to be used as a reference. The L* and b* values are obtained by placing samples (in powder form) in the glass cell (fill the cell to about a half) of the colorimeter and analyse the sample in accordance with the user's instructions of the colorimeter. The colorimeter used is a Minolta CR400 Colorimeter.

The invention will now be described with the help of the following examples and comparative experiments, without being however limited thereto.

EXAMPLES

Example 1

Approximately 500 g of 70% DS syrup of fructose 90% in purity were evaporated in a jacketed vessel under vacuum, at an absolute pressure of around 0.05 bar. The syrup was gently stirred by means of a blade propeller. The evaporation took place at 60° C. and the produced steam went into a cylindrical condenser, fitted with a coil internally refrigerated by a thermostatic fluid at −1° C. The condensed water fell down into a cylindrical vessel maintained a few degrees over 0° C. The collected water amount was evaluated by the liquid height in the vessel at the condenser bottom. After a few hours, when the DS percentage was around 94%, 35 g of fructose, in the size range 75-250 µm, were poured into the syrup in order to induce a partial crystallization of the amorphous fructose. 10 minutes later a small amount of the slurry, at semi-crystalline state, was withdrawn from the vessel, quenched over a cylinder internally refrigerated at a temperature around 2° C. Due to its very rapid cooling, said quenching, the fructose slurry immediately solidified. The obtained solid product appeared transparent and fragile. The solid was then put in a cylindrical container, at 2° C., where it was grinded down to particles between 500 µm and 2-3 mm Finally, the fructose particles were put over a vibrating surface where they were let to jump together with 35 g of fructose powder, in the size range 25-250 µm for 20 minutes. After the coating process the obtained fructose particles were separated from the coating powder by sieving. During this drying process, the temperature of the particles was naturally increased from a few degrees until the ambient temperature and there was a transition of the solid from the glassy state to the rubber state. This transition was accompanied by a further transformation of the amorphous fructose to the crystalline fructose. The produced particles, quite rounded and non-sticky, were saved in a sealed sample holder. After a period of time of 30 days the particles exhibited no agglomeration, very low fragility, thus their conditions appeared very stable. In Figure 1, the obtained semi-crystalline fructose having an average particle size of about 1.2 mm is shown.

Solubility rate tests of the produced semi-crystalline particles were performed by comparison with the solubility rate of the pure crystalline fructose. Two separate runs were carried out by using an initial mass of 1.5 g of fructose particles in the range size 425-600 µm. The solid was stirred in a cylindrical vessel with distilled water at ambient temperature. In both the runs the solid disappearance was detected after 25 s, showing a quite equal solubility rate of the produced semi-crystalline fructose with respect to the crystalline fructose.

Example 2

400 g of 70% DS syrup of fructose 87% in purity was evaporated as reported in Example 1, until a DS value equal approximately 94% was reached. Then, 28 g of pure fructose was seeded and mixed with the syrup for 10 minutes, when a homogeneous slurry was obtained. The flowability of the slurry appeared better with respect to that one of the slurry in Example 1, because of the presence of more than 5% of maltose, among the impurities. The presence of fructose powder induced a partial crystallization of the amorphous fructose. A sample of the slurry was withdrawn and laid over a cooled surface, internally refrigerated at around 2° C. The so-called semi-crystalline solid fructose at glassy state was removed from the cold surface and grinded in a refrigerated vessel, down to a size of a few mm. Then, the produced solid particles were let to jump with 30 g of fructose powder in the size range 25-250 µm for 20 minutes. At the end of the overall process the characteristics of the obtained particles resulted quite similar to those produced in Example 1.

Example 3

400 g of 70% DS syrup of fructose 87% in purity was evaporated as reported in Example 2, until a DS value equal approximately 94% was reached. Then 28 g of solid fructose produced in Example 2, sieved at a size less than 1.25 mm, were seeded to induce the partial crystallization of the amorphous fructose. After 10 minutes the agitation was stopped, and a sample of the slurry was put in contact with a cooled surface internally refrigerated at around 2° C. The quench of the slurry caused its sudden solidification at glassy state. The obtained solid was removed from the cooled surface and grinded in a refrigerated container down to a particle size of a few mm. The following coating process was performed by let the produced particles to jump over a vibrating surface together with 30 g of the fructose powder, as used for seeding. During the coating process the solid, lasted 15 minutes, the temperature rises from a few degrees ° C. up to ambient temperature. During this period of time the solid transition from glassy to rubber state occurred and a further crystallization of the fructose as well. At the end, the overall process the produced solid particles enough hard to be well handled during the storage, were separated from the coating powder by sieving.

After a storage of 30 days the solid particles appeared to preserve their original shape, to have a very good flowability and a good hardness.

Example 4

400 g of 70% DS syrup of fructose 87% in purity was evaporated as reported in Example 2, until a DS value equal approximately 94% was reached. Then 28 g of pure dextrose powder, 200 µm in size, were seeded to induce the partial crystallization of the amorphous fructose. After 10 minutes the agitation was stopped, and a sample of the slurry was put in contact with a cooled surface internally refrigerated at around 2° C. The quench of the slurry caused is sudden solidification at glassy state. The obtained solid was removed from the cooled surface and grinded in a refrigerated container down to a particle size of a few mm A coating was then performed by let the produced particles to jump over a vibrating surface together with 30 g of dextrose. During the dry process the solid, lasted 15 minutes, the temperature rises from a few degrees ° C. up to ambient temperature, dealing with its transition from glassy to rubber state and a further crystallization of the fructose. At the end of the overall process, the produced solid particles hard enough to be well and easily handled for and during storage, were separated from the coating powder by sieving.

After a storage of 30 days the solid particles appeared to preserve their original shape, to have a very good flowability and a good hardness.

Comparative Experiment 1

For the sake of comparison, an experiment was carried out according to the traditional prior art method to produce crystalline fructose by starting from the same raw material as in Example 1, that is a 70% DS syrup with 90% fructose purity.

Figure 2:
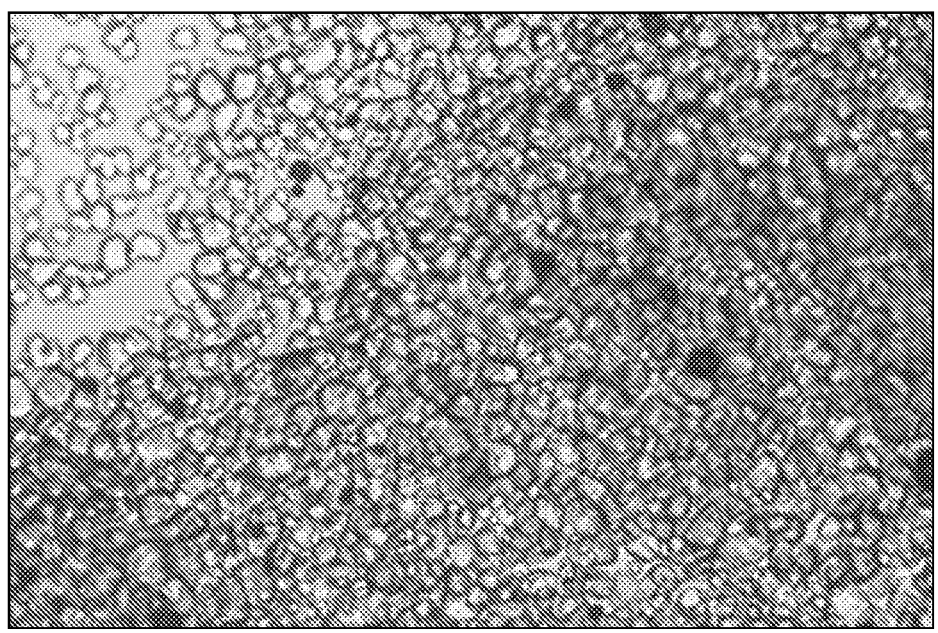
FIG. 2 is an image of the crystalline fructose produce by the prior art method.

The crystallization experiment was carried out firstly by evaporating the fructose syrup at 60° C. under vacuum until a DS value of 94% was reached. Then 10 wt % of pure fructose powder was added for seeding and the slurry was maintained under stirring for 20 minutes at constant temperature. The slurry within the vessel was then cooled during the night at ambient temperature, by simply stopping the circulation of the thermostatic stream trough the jacket. The slurry was filtered and the obtained crystals were dried. An image of the obtained crystals is provided in Figure 2. The average particle size was around 600 μm.

The collected mass of crystals (i.e. the yield) was less than 15% of the overall solute. In this case, the mother liquor needs to be recycled i.e. the process has to be repeated to extract and obtain more final product from the mother liquor, requiring high energy consumption and high costs.

On the contrary, the production process of the semi-crystalline fructose product according to the invention led directly to the fructose final product and no recycling streams were needed. In the process according to the invention, the production yield was equal to 100% of the solute fructose initially present in the syrup, whereas in the case of the process according to the prior art the yield was less than 15%.

Furthermore, there were differences in the duration of the process. In the process according to the invention, after the first evaporation, the fructose particles were obtained in less than 1 h (see Example 1), whereas the production of crystalline fructose according to the prior art required several hours.

Finally, the semi-crystalline fructose particles produced according to the inventive method can be immediately packaged. However, this is not the case of crystalline fructose produced according to the prior art, which requires further down-stream processing before packaging can take place, in particular the separation from the mother liquor, grinding and drying.

The invention claimed is:

1. A fructose in solid form comprising:
a matrix phase, and
a dispersed phase comprising a plurality of carbohydrate crystals dispersed within the matrix phase;
wherein the matrix phase comprises amorphous fructose and from at least 5 wt. % to at most 20 wt. % water relative to the total mass of the fructose;
wherein the carbohydrate crystals in the dispersed phase comprise fructose and optionally one or more other carbohydrate(s); and
wherein the fructose in solid form comprising the matrix phase and the dispersed phase comprising the plurality of carbohydrate crystals dispersed within the matrix is coated with a dry powder coating.

2. The fructose according to claim 1, wherein the dry powder coating is selected from sweeteners, starches, polyols, dextrins, and maltodextrins and mixtures thereof.

3. The fructose according to claim 2, wherein the plurality of carbohydrate crystals comprise fructose and one or more other carbohydrate(s), wherein the one or more other carbohydrate(s) are selected from sweeteners and polyols.

4. The fructose according to claim 2, wherein the plurality of carbohydrate crystals consist of fructose and wherein the fructose in solid form containing the matrix phase and the dispersed phase comprising the plurality of carbohydrate crystals dispersed within the matrix is coated with a dry powder coating that is different from fructose or does not consist of fructose.

5. The fructose according to claim 1, wherein the plurality of carbohydrate crystals comprise fructose and one or more other carbohydrate(s) are present, wherein the one or more other carbohydrate(s) are selected from sweeteners and polyols.

6. The fructose according to claim 5, wherein the one or more other carbohydrate(s) have a glass transition temperature (Tg) higher than the Tg of fructose.

7. The fructose according to claim 6, wherein the sweetener is selected from dextrose, sucrose, maltose, isomaltulose, lactose, raffinose and mixtures thereof and/or the polyol is selected from maltitol, isomalt, mannitol and mixtures thereof.

8. The fructose according to claim 1, wherein the plurality of carbohydrate crystals consist of fructose and wherein the fructose in solid form containing a matrix and a plurality of carbohydrate crystals dispersed within the matrix is coated with a dry powder coating that is different from fructose or does not consist of fructose.

9. The fructose of claim 1, wherein the matrix phase is present in an amount of at least 85% dry substance content (DS).

10. The fructose of claim 1,
wherein the amorphous fructose is present in an amount of at least 0.1 wt % relative to the total mass of the fructose; and
wherein the dispersed phase is present in an amount of at least 20 wt % relative to the total mass of the fructose.

11. The fructose of claim 1, wherein the fructose is in the form of a powder comprising particles having a D50 of at least 10 μm.

12. The fructose of claim 11, wherein the dry powder coating contains coating particles, said coating particles having a D50 that is at least 15% smaller than the D50 of the particles forming the powder.

13. The fructose of claim 1 having one or more of:
a solubility of at least 700 g/l;
a CIELAB L* value of at least 85;
a flowability between 20 and 45 degrees;
a hydrophilicity between 15% and 50%.

14. A powder containing the fructose of claim 1.

15. The fructose according to claim 1, wherein the matrix phase comprises from at least 5 wt. % to at most 10 wt. % water relative to the total mass of the fructose.

16. A method of manufacturing the fructose in solid form according to claim 1 comprising:
(i) Providing an aqueous fructose solution having a dry substance (DS) of at least 80 wt % relative to the total mass of the solution;
(ii) Providing a powder containing particles comprising a carbohydrate material;

(iii) Adding the powder to the aqueous fructose solution to obtain an aqueous slurry having a glass transition temperature ($T_g$);
(iv) Quick cooling the aqueous slurry to a temperature of at most the $T_g$ of said slurry thereby obtaining a product containing solidified fructose;
(v) Optionally milling the product containing the solidified fructose and/or coating the solidified fructose or the milled solidified fructose.

* * * * *